US006872695B1

(12) United States Patent
Groemminger et al.

(10) Patent No.: US 6,872,695 B1
(45) Date of Patent: Mar. 29, 2005

(54) METHOD FOR IN-EYE CLEANING OF CONTACT LENS COMPRISING POLYMERIC BEADS

(75) Inventors: Suzanne F. Groemminger, Rochester, NY (US); Joseph C. Salamone, Boca Raton, FL (US)

(73) Assignee: Bausch & Lomb Incorporated, Rochester, NY (US)

(*) Notice: Subject to any disclaimer, the term of this patent is extended or adjusted under 35 U.S.C. 154(b) by 49 days.

(21) Appl. No.: 09/684,191

(22) Filed: Oct. 6, 2000

(51) Int. Cl.$^{7}$ .................................................. A61K 7/00

(52) U.S. Cl. ....................... 510/112; 510/113; 510/475; 510/477

(58) Field of Search ................................ 510/112, 113, 510/475, 476, 477

(56) References Cited

U.S. PATENT DOCUMENTS

| | | | | |
|---|---|---|---|---|
| 2,979,528 | A | 4/1961 | Lundsted et al. | 260/584 |
| 3,583,957 | A | 6/1971 | Chromecek et al. | 260/86.1 |
| 4,394,179 | A | 7/1983 | Ellis et al. | 134/7 |
| 4,493,783 | A | 1/1985 | Su et al. | 252/174.23 |
| 4,525,346 | A | 6/1985 | Stark | 424/80 |
| 4,534,878 | A | 8/1985 | Ellis et al. | 252/173 |
| 4,613,379 | A | 9/1986 | Su et al. | 134/7 |
| 4,655,957 | A | 4/1987 | Chromecek et al. | 252/174.23 |
| 4,670,060 | A | 6/1987 | Su et al. | 252/174.17 |
| 4,792,414 | A | 12/1988 | Su et al. | 252/174.17 |
| 4,820,352 | A | 4/1989 | Riedhammer et al. | 134/30 |
| 4,830,783 | A | 5/1989 | Ellis et al. | 252/545 |
| 4,870,145 | A | 9/1989 | Chromecek | 526/217 |
| 5,017,238 | A | 5/1991 | Chromecek et al. | 134/7 |
| 5,037,484 | A | 8/1991 | Su et al. | 134/7 |
| 5,070,215 | A | 12/1991 | Bambury et al. | 556/418 |
| 5,089,053 | A | 2/1992 | Chou et al. | 134/7 |
| 5,190,594 | A | 3/1993 | Chou et al. | 134/6 |
| 5,310,429 | A | 5/1994 | Chou et al. | 134/6 |
| 5,415,837 | A | 5/1995 | Schäferet al. | 422/28 |
| 5,532,224 | A | 7/1996 | Desai | 514/63 |
| 5,580,392 | A | 12/1996 | Sulc | 134/7 |
| 5,604,189 | A | 2/1997 | Zhang et al. | 510/112 |
| 5,610,252 | A | 3/1997 | Bambury et al. | 526/279 |
| 5,627,214 | A | 5/1997 | Schäfer et al. | 514/642 |
| 5,631,005 | A | 5/1997 | Dassanayake et al. | 424/78.04 |
| 5,654,262 | A | 8/1997 | Desai et al. | 510/115 |
| 5,719,110 | A | 2/1998 | Cook | 510/112 |
| 5,765,579 | A | 6/1998 | Heiler et al. | 134/42 |
| 5,773,396 | A | 6/1998 | Zhang et al. | 510/115 |
| 5,858,937 | A | 1/1999 | Richard et al. | 510/112 |
| 5,900,213 | A | 5/1999 | Dassanayake et al. | 422/28 |
| 5,919,742 | A | 7/1999 | Tsuzuki | 510/112 |

FOREIGN PATENT DOCUMENTS

| | | | |
|---|---|---|---|
| EP | 0372427 | 1/1989 | C11D/3/37 |
| GB | 2188744 | 7/1987 | G02C/13/00 |
| WO | 00/37049 | 6/2000 | A61K/9/08 |

*Primary Examiner*—Necholus Ogden
(74) *Attorney, Agent, or Firm*—Robert B. Furr, Jr.; Denis A. Polyn; Rita D. Vacca

(57) ABSTRACT

An in-eye method for cleaning contact lenses comprises use of a cleaner using water-containing beads. The water-containing beads are prepared such that the bead size is smaller than the punctual opening. They are easily flushed from the ocular environment by normal tear flow. The cleaner may also be used to clean contact lenses, with the cleaner applied directly to the lens and digitally rubbed to remove accumulated debris on the lens.

4 Claims, No Drawings

METHOD FOR IN-EYE CLEANING OF CONTACT LENS COMPRISING POLYMERIC BEADS

FIELD OF THE INVENTION

The present invention relates to a composition and method of cleaning contact lenses. More specifically, the invention relates to a composition useful for in-eye cleaning of contact lenses.

BACKGROUND OF THE INVENTION

Contact lenses need to be periodically treated, for example, disinfected, cleaned soaked and the like, because of the tendency for a variety of microbes and other materials to accumulate on the lenses. An efficacious disinfecting/cleaning regimen removes these accumulations and provides a contact lens that is safe and comfortable to wear.

Rigid, gas permeable and soft materials are produced from different materials having different chemical and physical properties. Lenses made from these different materials tend to accumulate different types of deposits. Because different lenses tend to accumulate different types of deposits, it is difficult to formulate a cleaner that is effective against all of the deposits, especially those deposits that are proteinaceous or sebaceous.

Conventional contact lens cleaning solutions contain one or two general classes of cleaners. Surfactant cleaners, generally known as daily cleaners because of their recommended daily use, are effective for the removal of most carbohydrate and lipid (sebaceous) materials. Enzymatic cleaners, on the other hand, contain proteolytic enzymes and are typically recommended for weekly use to remove proteinaceous material such as lysozyme.

Rigid gas-permeable (RGP or "hard") contact lenses and hydrogel ("soft") contact lenses require different types of cleaners. Daily cleaners for RGP contact lenses usually contain both a surfactant and a mechanical abrasive. The user cleans the RGP lenses by rubbing the lens with the cleaning composition to remove the debris. Combinations of surface active agents and mechanical cleaners are disclosed in U.S. Pat. No. 4,394,179 to Ellis et al.

A typical method for daily cleaning contact lenses comprises the steps of:

(1) removing the contact lens from the eye;

(2) applying a cleaner to the contact lens;

(3) rubbing the contact lens with the cleaner; and (4) rinsing the contact lens.

Rinsing solutions are normally used to remove any cleaner left on the lens after cleaning. The rinsing solution must also be compatible with the ocular environment as some solution will remain on the lens and be transferred into the eye when the lens is inserted.

With conventional abrasive cleaners, the lens needs to be thoroughly rinsed to avoid carrying residual amounts of cleaner into the eye. Conventional abrasive cleaners need to be removed from the lens before placing the lens in the eye because conventional abrasive cleaners can cause both mechanical abrasion and chemical irritation if placed in the eye. Aqueous suspensions of polymeric beads such as those disclosed in U.S. Pat. No. 4,655,957 to Chromececk and European Patent Application No. 0 063 472 to Su have proven to be effective cleaning agents for removing deposits on contact lenses. In particular, U.S. Pat. No. 4,655,957 discloses an aqueous suspension having 0.001 to 25 weight percent of a particulate hydrophilic polymer in a buffered, isotonic solution containing one or more surfactants and optional preserving and sequestering agents.

European Patent Application No. 0 063 472 discloses a cleaner which comprises a suspension containing a particulate organic polymer or polysiloxane of a hydrophobic, thermoplastic nature.

European Patent Application No. 0 063 472 and U.S. Pat. Nos. 4,613,379; 4,670,060; 4,792,414; and 5,037,484 (all to Su et al.) disclose a composition and method for cleaning contact lenses with a particulate organic polymer or polysiloxane with a carrier. The particulate polymer is selected from the group consisting of organic polymers, polysiloxane polymers and mixtures thereof. The polysiloxane is of a hydrophobic, thermoplastic nature. The resulting composition is compatible with ocular tissue and has a viscosity sufficient to keep the particulate polymer suspended within the carrier. The particulate polymers should have a degree of hardness and shape so as to be effective as a cleaning agent but yet not have the ability to scratch the lens.

Abrasive cleaners need to remove deposits from contact lenses without scratching the surface of the lenses. The abrasive beads used in the abrasive cleaner may be hydrophobic or hydrophilic. Conventional hydrophobic beads tend to have higher surface hardness and bulk rigidity than hydrophilic beads. Conventional hydrophilic beads, while softer and less likely to scratch the surface of the contact lens, tend to agglomerate and sink out of suspension. Thus they tend to fall on the bottom and eventually cake together, requiring the consumer to vigorously shake the bottle to re-suspend the beads

SUMMARY OF THE INVENTION

This invention provides a method and composition for cleaning contact lenses. In one embodiment, the invention provides a method for cleaning contact lenses while the lenses are being worn in the eye.

In another embodiment, the invention provides a composition for cleaning contact lenses using water-containing abrasive beads. The composition overcomes the problem of sedimentation previously associated with the use of hydrophilic abrasive beads. In accordance with the invention, it has been found that controlling the size of the bead agglomeration as claimed surprisingly inhibits their sedimentation and permits the beads to stay suspended in solution. Additionally, by controlling the initial size of the abrasive bead agglomerates as claimed, the further extent of agglomeration appears to also be inherently controlled such that the agglomerations themselves have diameters that allow the beads to be compatible with ocular installation and to be flushed from the eye by normal tear flow. The cleaning composition may also be used with digital cleaning of a contact lens. While not to limit the scope of the invention by a recitation of theory, it is believed that the water-containing beads of the invention are themselves agglomerations of smaller beads that retain water in the interstitial spaces between the smaller beads that make up the agglomerated beads. Surprisingly, it has been found that the process set out in the Examples provides bead products that agglomerate to form water-containing beads as claimed. These water-containing beads surprisingly agglomerate to form useful particle sizes without the problem of excessive agglomeration associated with conventional hydrophilic beads.

The composition of cleaner may also comprise a thickening agent, at least one surfactant, a cleaner, and a preservative. The abrasive water-containing beads ("abrasive cleaner" or "beads") preferably consists of polyHEMA

[poly(2-hydroxyethyl methacrylate)] beads that form agglomerations less than 100 microns in diameter, preferably less than 50 microns. The agglomerated beads may contain from about 10 to about 90 weight percent water, preferably 20 to 80 weight percent water and more preferably 40 to 60 weight percent water.

The invention provides a composition for cleaning contact lenses, which composition comprises water-containing beads having a mean particle size of less than 100, wherein at least 75 weight percent of said water-containing beads have a major diameter of less than 50 $\mu$m. In a preferred embodiment, the water-containing beads have a mean particle size of less than 50 and at least 75 weight percent of the water-containing beads have a major diameter of less than 30 $\mu$m. In a more preferred embodiment, the water-containing beads have a mean particle size of less than 40, wherein at least 75 weight percent of said water-containing beads have a major diameter of less than 30 $\mu$m. The composition of the invention may suitably comprise other ophthalmically compatible components including thickening agents and/or surfactants.

The beads are preferably a polyHEMA material of the composition taught in U.S. Pat. No. 4,655,957 to Chromecek et al., and may suitably comprise from about 0.05 to about 1.5 weight percent of the composition. In a preferred embodiment, the water-containing beads are present in the amount of from about 0.1 to about 1.0 weight percent of the solution composition, more preferably from about 0.25 to about 0.75 weight percent of the solution composition, and most preferably from about 0.4 to about 0.6 weight percent of the solution composition.

The solution composition may also contain one or more preservatives and thickening agents. PAPB is a preferred preservative. Carboxy vinyl polymers are suitable thickening agents, and carbomers (polymers of acrylic acid crosslinked with allyl sucrose) are preferred thickening or gelling agents. In one preferred embodiment, the thickening agent comprises at least one selected from the group consisting of poly(ethylene glycol) with a molecular weight distribution of from about 400 to about 4000, poly (ethylene oxide) hydroxyethyl cellulose, methyl cellulose, hydroxypropyl cellulose, hydroxypropyl methyl cellulose, sodium carboxymethyl cellulose, HEMA, poly(vinyl alcohol), and poly(N-vinylpyrrolidone) (PVP).

In another embodiment, the invention provides a method of cleaning a contact lens in the eye of a wearer comprising applying to said contact lens an ophthalmically compatible contact lens cleaning solution comprising water-containing beads having a mean particle size of less than 30, wherein at least 90 weight percent of said water-containing beads have a major diameter of less than 50 $\mu$m. The method of the invention may further comprise the sequential steps of blinking and then rinsing the eye and the contact lens with an ophthalmic rinsing solution to dilute or substantially remove the contact lens cleaning solution from the eye. In a preferred embodiment, no rinsing step is needed, and the method is carried out in the absence of a rinsing step.

DETAILED DESCRIPTION OF THE INVENTION

The present invention can be used with all contact lenses such as conventional hard, soft, rigid and soft gas permeable, and silicone (including both hydrogel and non-hydrogel) lenses, but is preferably employed with soft lenses. The composition and preparation of the polymeric beads are disclosed in U.S. Pat. No. 4,870,145 to Chromecek. The '145 Chromecek patent is incorporated herein by reference in its entirety, and specifically for a description the process for preparing water-containing polymeric beads.

This invention provides a process of making water-containing polymeric beads that not only makes the beads less susceptible to excessive agglomeration but also permits the beads to be used with a contact lens that is being worn in the eye. Surprisingly, it has been found that controlling the particle size of the beads in accordance with the invention limits the ultimate size of bead agglomerations within the solution. Thus the invention surprisingly controls agglomeration such that the agglomerated beads are still small enough to easily be washed from the surface of the contact lens and flushed from the eye through the lacrimal puncta by the normal flow of tear fluid.

In one embodiment, the composition of the invention is a sterile, aqueous solution that comprises:

a) a thickening agent;

b) at least one surface active agent;

c) a cleaner;

d) a preservative; and e) an abrasive cleaner consisting of polyHEMA beads and/or HEMA copolymers wherein said beads form agglomerations less than 100 microns in diameter, preferably less than 50 microns.

The thickening agent may optionally comprise a gel matrix carrier being either a pseudoplastic (viscosity affected by shear-liquification of gel upon blinking) such as xanthan gum, or a material which is affected by the ionic strength of tears causing the gel matrix to collapse, such as the Carbomer type gelling agents (i.e., Carbopol)

Thickening agents can include carboxy vinyl polymers of high molecular weight such as the Carbomer type gelling agents (i.e., Carbopol available from B. F. Goodrich Chemical Co.), poly(ethylene glycol) with a molecular weight distribution of 400 to 4000, poly(ethylene oxide), methyl cellulose, hydroxyethyl cellulose, hydroxypropyl cellulose, hydroxypropyl methyl cellulose, sodium carboxymethyl cellulose, low molecular weight HEMA, poly(vinyl alcohol), and PVP to form a suspension. The end product may be a fluid or may be a gel.

The composition may further include other surface-active agents having cleaning activity for contact lenses. A wide variety of surface active agents are known in the art as cleaning agents, including anionic, cationic, nonionic and amphoteric surface active agents.

Representative anionic surface-active agents include sulfated and sulfonated surface active agents, and physiologically acceptable salts thereof, which provide good cleaning activity for lipids, proteins, and other contact lens deposits. Examples include sodium lauryl sulfate, sodium laureth sulfate (sodium salt of sulfated ethoxylated lauryl alcohol), ammonium laureth sulfate (ammonium salt of sulfated ethoxylated lauryl alcohol), sodium trideth sulfate (sodium salt of sulfated ethoxylated tridecyl alcohol), sodium dodecylbenzenesulfonate, disodium lauryl or laureth sulfosuccinate (disodium salt of a lauryl or ethoxylated lauryl alcohol half ester of sulfosuccinic acid), disodium oleamido sulfosuccinates, and dioctyl sodium sulfosuccinate (sodium salt of the diester of a 2-ethylhexyl alcohol and sulfosuccinic acid).

Nonionic surface active agents having good cleaning activity include certain polyoxyethylene, polyoxypropylene block copolymer (poloxamine) surface active agents, including various surface active agents available under the trade name Tetronic from BASF Corp., e.g., Tetronic 1107. Other representative nonionic surface active agents include: ethoxylated alkyl phenols, such as various surface active agents available under the tradenanes Triton (Union Carbide, Tarrytown, N.Y., USA) and Igepal (Rhone-Poulenc, Cranbury, N.J., USA); polysorbates such as polysorbate 20, including the polysorbate surface active agents available under the tradename Tween (ICI Americas, Inc., Wilmington, Del., USA); and alkyl glucosides and polyglucosides such as products available under the tradename Plantaren (Henkel Corp., Hoboken, N.J., USA).

The composition may include a cationic surface-active agent. Representative cationic surface agents include triquatemary phosphate esters, such as various cationic surface active agents available from Mona Industries, Inc., Patterson, N.J., USA under the tradename Monaquat.

Additionally, the composition may include an amphoteric surface-active agent. Amphoteric surface active agents include fatty acid amide betaines, such as the cocoamidoalkyl betaines available under the tradename Tego-Betain (Goldschmidt Chemical Corp., Hopewell, Va., USA). Other amphoterics include imidazoline derivatives such as cocoamphopropionates available under the tradename Miranol (Rhone-Poulenc), and n-alkylamino acids under the name gradename Mirataine (Rhone-Poulenc).

Preferred surfactants are neutral or nonionic surfactants which may be present in amounts up to about 5% (w/v), preferably up to about 3% (w/v) and more preferably up to about 1% (w/v). Examples of suitable surfactants include but are not limited to: polyethylene glycol esters of fatty acids, polyoxypropylene ethers of $C_{12}$–$C_{18}$ alkanes and polyoxyethylene-polyoxypropylene block copolymers of ethylene diamine (i.e., poloxamine). Additionally, surfactants such as Pluronic (Wyanclotte Chemicals Co.), Tween (Atlas Powder Company) or tyloxapol may be added.

In the preferred embodiment, the composition comprises at least one non-ionic surfactant. In particular, the composition preferably comprises a block copolymer adduct of ethylene diamine. The surfactant is a poly(oxypropylene)-poly(oxyethylene) block copolymer adduct of ethylene diamine having a molecular weight from about 10,000 to about 20,000 where at least 40 weight percent, and more particularly, from about 40 to about 80 weight percent of the surfactant is poly(oxyethylene). More preferably, the poly (oxypropylene)-poly(oxyethylene) block copolymer adduct will have a molecular weight ranging from about 12,000 to about 19,000 where at least 60 weight percent, and more particularly, from about 60 to 80 weight percent of the adduct is poly(oxyethylene).

The foregoing surfactants are further described with methods for their manufacture in U.S. Pat. No. 2,979,528. They are also known by the generic name—poloxamine—and are commercially available from BASF-Wyandotte under the registered trademark "Tetronic." The preferred embodiment comprises Tetronic 1107.

The composition may include a non-amine polyethyleneoxy-containing material in addition to the above named surfactants. In addition to homopolymers of polyethylene glycol or polyethyleneoxy, representative PEO-containing materials include certain polyethyleneoxy-polypropyleneoxy block copolymers, also known as poloxamers. Such materials are commercially available under the tradename Pluronic from BASF Corporation, Parsippany, N.J., USA, and include Pluronic Y108 and F127. Other suitable PEO-containing materials include ethoxylated glucose derivatives, such as methyl gluceth-20 including the product available as Glucam E-20 (Amerchol Corp., Edison, N.J., USA). Other nonionic ethers of sorbitol or glycerol include products available under the tradename Ethosperse, including sorbeth-20 supplied as Ethosperse SL-20 and glycereth-26 supplied as Ethosperse G-26 (Lonza Inc., Fair Lawn, N.J., USA). A preferred PEO-containing material is glueth-10 available as Glucam E-10.

It is preferred that the composition comprises at least one, preferably two surface-active agents. In particular, it is preferred that the composition comprises Tetronic 1107 and Glucam E-10 in total concentration of from about 0.1 to about 1.0 weight percent, preferably about 0.5 weight percent.

In addition to the surface-active agents just described, other cleaners may be incorporated into the composition. In particular, a phosphonic acid, or a physiologically compatible salt thereof as disclosed in U.S. Pat. No. 5,858,937, the entire disclosure herewith incorporated by reference, may be included. A particularly preferred species is the tetrasodium salt of 1-hydroxyethylidene-1,1-diphosphonic acid, also referred to as tetrasodium etidronate, commercially available from Monsanto Company under the tradename of DeQuest® 2016 diphosphonic acid sodium salt or phosphonate. Suitable concentrations for these phosphonic acids are in the range of from about 0.01 to about 0.50 weight percent, preferably about 0.1 weight percent.

The subject cleaner preferably includes at least one antimicrobial agent. As used herein, the term antimicrobial agent is intended to mean non-oxidative organic chemicals that derive their antimicrobial activity through a chemical or physicochemical interaction with organisms. An antimicrobial agent is included in an amount effective to at least inhibit growth of microorganisms in the composition. Various antimicrobial are known in the art as useful in contact lens solutions including: quaternary ammonium salts such as Polyquatemium 1® from ONYX Corporation; benzalkonium chloride; chlorhexidine (1,1-hexamethylbis[5-(p-chlorophenyl)biguanide]) or water soluble salts thereof, such as chlorhexidine gluconate; and preferrably polyhexamethylene biguanide (a polymer of hexamethylene biguanide, also referred to as polyaminopropyl biguanide, available from Zeneca, Wilmington, Del.) or water soluble salts thereof, such as the polyhexamethylene biguanide hydrochloride available under the trade name Cosmocil CQ (ICI Americas Inc.). Combinations of antimicrobial agents may also be employed. If used in the cleaner, the antimicrobial agent should be used in an amount that will at least partially reduce the microorganism population in the formulations employed. Typically, antimicrobial agent are present in concentration ranging from about 0.00001% (w/v) to about 5% (w/v), depending on the specific agent. More preferably, the antimicrobial agent is present from about 0.00003% (w/v) to about 0.05% (w/v).

Additionally, the cleaner may include a sequestering agent (EDTA), an osmolality adjusting agent and a pH adjuster for the gelling agent (i.e. NaOH). In a preferred embodiment, the osmolality-adjusting agent is glycerol in concentration sufficient to provide osmolality of 270 mOsm/Kg, and the pH is adjusted by adding 1N NaOH sufficient to provide a solution pH of about 5–6.

Examples of preferred sequestering/chelating agents include ethylene diaminetetraacetic acid (EDTA) and its salts (sodium) which are normally employed in amounts from about 0.024 to about 2.0% (w/v). Other known sequestering agents such as certain poly(vinyl alcohol)s can also be used.

Typically, the cleaner of the present invention is adjusted with tonicity agents to approximate the osmotic pressure of normal lacrimal fluids which is equivalent to a 0.9 percent solution of sodium chloride or 2.5 percent gylcerol solution.

Examples of suitable tonicity adjusting agents include, but are not limited to: sodium and potassium chloride, dextrose, glycerin, calcium and magnesium chloride. These agents are typically used in amounts ranging from about 0.01 to 2.5% (w/v) and preferably, from 0.2 to about 1.5% (w/v). Preferably, the tonicity agent will be employed in an amount to provide a final osmotic value of 200 to 450 mOsm/kg and more preferably between about 250 to about 350 mOsm/kg, and most preferably between about 280 to about 320 mOsm/kg.

The pH of the present invention should be maintained within the range of 5.0 to 8.0, more preferably about 6.0 to 8.0, most preferably about 6.8 to about 7.8.

As previously mentioned, the present invention can be used with all contact lenses such as conventional hard, soft (water-containing), rigid and soft gas permeable, and silicone (including both hydrogel and non-hydrogel) lenses. Preferably the cleaner is employed with hydrogel lenses. Such lenses absorb significant amounts of water such as from about 4 to about 80 percent by weight. Lens materials include those prepared from monomers such as 2-hydroxyethyl acrylate, 2-hydroxyethyl methacrylate, N-vinylpyrrolidone, glycerol methacrylate, methacrylic acid or other acid esters. Preferred materials include those disclosed in U.S. Pat. Nos. 5,610,252 and 5,070,215 (both Bambury et al., assigned to Bausch & Lomb Incorporated), the entire disclosures which are herewith incorporated by reference.

The composition of the invention can be used as a conventional abrasive contact lens cleaning solution. Cleaning can be achieved if a few drops of the cleaner are initially placed on each side of the lens, and the lens is rubbed for a period of time, for example, approximately 20 seconds. The lens can then be rinsed with a rinsing solution such as saline.

This invention is particularly useful for extended wear lenses or those lenses which are worn for long periods of time without removal for cleaning. In another embodiment of the invention, a few drops of the cleaner may be instilled directly into the eye. As the cleaner spreads over the lens, the contact lens wearer blinks. The blinking action causes the water-containing beads in the solution to mechanically clean debris from the lens surface. As the hydrogel bead agglomerations are small, the beads do not irritate the ocular environment and are easily flushed by the tear flow through the lacrimal puncta Alternately, an eye rinsing solution may be used to flush any residue cleaner from the eye region.

EXAMPLE 1

100 ml of technical grade xylene was placed into a 1 liter round bottom reaction flask fitted with a reflux condenser and purged with nitrogen. 2-Hydroxyethyl methacrylate copolymer beads were prepared by dissolving 8 g 2-hydroxyethyl methacrylate, 2 g ethylene glycol dimethacrylate and 2 g methyl methacrylate into the reaction vessel. The resulting solution was thoroughly mixed. 100 $\mu$l of tert butyl peroxide was added to the mixture. The mixture was stirred, heated to 80° C. and refluxed. Once a precipitate starts to form, the mixture is continuously stirred and removed from heat. Once the mixture reaches room temperature, the excess xylene is filtered off. The filtrate is washed with hexane and dried in an oven 12–18 hours at 60° C.

EXAMPLES 2–4

A base formulation was prepared having 20% glycerin, 0.025% EDTA, 0.5% Glucam E-10, 0.010% DeQuest 2016, water and sufficient 1N NaOH to neutralize the carbomer material used to form a gel.

To an aliquot of the base formulation was added increasing concentrations of Carbopol 974P to evaluate the gel formation characteristics.

| Example Number | Formulation | Results |
|---|---|---|
| Example 2 | 0.2% Carbopol 974P plus base | Soupy |
| Example 3 | 0.5% Carbopol 974P plus base | Runny |
| Example 4 | 1% Carbopol 974P plus base | Gel-like |

EXAMPLE 5–11

A formulation was prepared containing the following constituents.

| Ingredient | Weight Percent |
|---|---|
| Carbopol 974P | 1.0 |
| Glycerol | 2.0 |
| Tetronic 1107 | 0.5 |
| Disodium edetate | 0.025 |
| DeQuest 2016 | 0.10 |
| PolyHEMA beads (prepared in accordance with Example 1) | 0.5% |
| 1N NaOH | PRN |
| Water | Qs 100% |

The sample was homogenized using a Gifford-Wood bench-top homogenizer, set at approximately 4500 rpm. Samples were removed to evaluate the extent of homogenization need to reduce the agglomerated particle size. The mean particle size was determined using a Coulter LS Particle Size Analyzer.

| Example Number | Homogenization Time - Minutes | Mean Particle Size/ Percent less than 50 $\mu$m |
|---|---|---|
| 5 | initial | 139.4 microns/54.1% |
| 6 | 1 minute | 69.8 microns/54.3% |
| 7 | 2 minutes | 69.9 microns/52.3% |
| 8 | 3 minutes | 68.7 microns/51.8% |
| 9 | 5 minutes | 56.8 microns/57.6% |
| 10 | 10 minutes | 46.1 microns/65.5% |
| 11 | 20 minutes | 13.3 microns/92.1% |

We claim:

1. A method of cleaning a contact lens in the eye of a wearer comprising applying to said contact lens an ophthalmically compatible contact lens cleaning solution comprising water-containing beads having a mean particle size of less than 30 $\mu$m but greater than about 13 $\mu$m, wherein at least 90 weight percent of said water-containing beads have a major diameter of less than 50 $\mu$m.

2. The method of claim 1 wherein said ophthalmic solution further comprises at least one surfactant.

3. The method of claim 2 wherein said method further comprising the sequential steps of blinking and then rinsing the eye and the contact lens with an ophthalmic rinsing solution to dilute or substantially remove the contact lens cleaning solution from the eye.

4. The method of claim 2 wherein said method is carried out in the absence of a rinsing step.

* * * * *